(12) United States Patent
S et al.

(10) Patent No.: US 10,429,356 B2
(45) Date of Patent: Oct. 1, 2019

(54) METHOD AND SYSTEM FOR CALIBRATING AN ULTRASONIC WEDGE AND A PROBE

(75) Inventors: Anandamurugan S, Bangalore (IN); Matthias Jobst, Dusseldorf (DE); Jerome Poirier, Forges les Bains (FR)

(73) Assignee: General Electric Company, Schenectady, NY (US)

( * ) Notice: Subject to any disclaimer, the term of this patent is extended or adjusted under 35 U.S.C. 154(b) by 1606 days.

(21) Appl. No.: 13/362,585

(22) Filed: Jan. 31, 2012

(65) Prior Publication Data
US 2013/0192334 A1    Aug. 1, 2013

(51) Int. Cl.
*G01N 29/30* (2006.01)
*G01N 29/06* (2006.01)
*G01N 29/24* (2006.01)
*G01N 29/26* (2006.01)

(52) U.S. Cl.
CPC ......... *G01N 29/30* (2013.01); *G01N 29/0645* (2013.01); *G01N 29/2487* (2013.01); *G01N 29/262* (2013.01)

(58) Field of Classification Search
CPC ............... G01N 29/30; G01N 29/0645; G01N 29/2487; G01N 29/262
See application file for complete search history.

(56) References Cited

U.S. PATENT DOCUMENTS

| | | | |
|---|---|---|---|
| 6,789,427 B2 | 9/2004 | Batzinger et al. | |
| 6,938,457 B2 | 9/2005 | Johnson et al. | |
| 2002/0045830 A1* | 4/2002 | Powers | A61B 8/06 600/459 |
| 2007/0000328 A1* | 1/2007 | Buttram | 73/597 |
| 2007/0068253 A1 | 3/2007 | Carodiskey | |
| 2010/0242613 A1* | 9/2010 | Simard et al. | 73/641 |
| 2011/0239768 A1 | 10/2011 | Berke et al. | |
| 2011/0247417 A1 | 10/2011 | Oberdoerfer et al. | |

* cited by examiner

*Primary Examiner* — Janet L Suglo
(74) *Attorney, Agent, or Firm* — Mintz Levin Cohn Ferris Glovsky and Popeo, P.C.

(57) ABSTRACT

A method and system for calibrating an ultrasonic wedge and a probe are disclosed. The calibration method includes the steps of automatically determining the ultrasonic signal acquisition width and the first ultrasonic signal gate based on the theoretical parameters of the ultrasonic wedge and the probe. The calibration method can also include the steps of automatically determining the operating status of transducer elements in a phased array transducer and then determining the actual parameters of the ultrasonic wedge based on the live transducer elements.

19 Claims, 4 Drawing Sheets

METHOD AND SYSTEM FOR CALIBRATING AN ULTRASONIC WEDGE AND A PROBE

BACKGROUND OF THE INVENTION

The subject matter disclosed herein relates to ultrasonic testing, and more particularly, a method and system for calibrating an ultrasonic wedge and a probe.

Nondestructive testing devices can be used to inspect test objects to identify and analyze anomalies in the objects. Nondestructive testing allows an inspection technician to maneuver a probe at or near the surface of the test object in order to perform testing of both the object surface and underlying structure. Nondestructive testing can be particularly useful in some industries, e.g., aerospace, power generation, and oil and gas transport or refining, where inspection of test objects must take place without removal of the object from surrounding structures, and where hidden anomalies can be located that would otherwise not be identifiable through visual inspection.

One example of nondestructive testing is ultrasonic testing. When conducting ultrasonic testing, an ultrasonic pulse can be emitted from an ultrasonic transducer of a probe and passed through a test object. Electric pulses can be generated by a transmitter and can be fed to the probe where they can be transformed into ultrasonic pulses by ultrasonic transducers. One type of ultrasonic transducer—a phased array transducer—comprises a plurality of electrically and acoustically independent transducer elements that incorporate piezoelectric ceramics. During operation, an electrical waveform pulse is applied to the electrodes of the each of the phased array transducer elements of the probe causing a mechanical change in the condition of the piezoelectric ceramic and generating an acoustic wave that can be transmitted through a material such as a metal or plastic to which the probe is coupled. Conversely, when an acoustic wave reflected from the material under inspection contacts the surface of the piezoelectric ceramic of a phased array transducer element, it generates a voltage difference across the electrodes that is detected as a receive signal by signal processing electronics.

As the ultrasonic pulses pass through the object, various pulse reflections called echoes occur as the pulse interacts with internal structures within the test object and with the opposite side (back wall) of the test object. The echo signals can be displayed on the screen with echo amplitudes appearing as vertical traces and time of flight or distance as horizontal traces. By tracking the time difference between the transmission of the electrical pulse and the receipt of the electrical signal, and measuring the amplitude of the received acoustic wave, various characteristics of the material can be determined. Thus, for example, ultrasonic testing can be used to determine material thickness or the presence and size of anomalies within a given test object.

In some applications, e.g., when testing pipe welds, the probe can be mounted on an ultrasonic wedge that provides intermediary physical contact between the phased array transducer and the test object. In order to conduct the ultrasonic inspection of the test object, it is necessary to "set up" the inspection, including the calibration of the probe and ultrasonic wedge combination. This calibration procedure requires the ultrasonic technician to use the geometric and physical properties of the ultrasonic wedge and the phased array transducer of the probe to determine the ultrasonic signal acquisition width and the start and stop times for the ultrasonic signal gate during the calibration procedure.

The calibration procedure uses theoretical parameters of the particular phased array transducer of the probe and the ultrasonic wedge to make these determinations, which might vary from actual conditions. For example, if the phased array transducer has elements that are not operating properly or the ultrasonic wedge experienced wear that changes its geometry, the calibration, and therefore subsequent ultrasonic measurements, will be inaccurate based on the difference between the theoretical and the actual values of the parameters of the components. Given the complexity of these determinations made during the calibration procedure, the inspection technician conducting the calibration procedure must typically have a high level of ultrasonic expertise.

The discussion above is merely provided for general background information and is not intended to be used as an aid in determining the scope of the claimed subject matter.

BRIEF DESCRIPTION OF THE INVENTION

A method and system for calibrating an ultrasonic wedge and a probe are disclosed. The calibration method includes the steps of automatically determining the ultrasonic signal acquisition width and the first ultrasonic signal gate based on the theoretical parameters of the probe and the ultrasonic wedge. The calibration can also include the steps of automatically determining the operating status of transducer elements in a phased array transducer and then automatically determining the actual parameters of the probe and the ultrasonic wedge based on the live transducer elements.

An advantage that may be realized in the practice of some disclosed embodiments of the method for calibration is to simplify the calibration method and avoid the need for an inspection technician with a high level of ultrasonic skill and knowledge, while providing more accurate calibration and subsequent ultrasonic measurements.

In one embodiment, a system for calibrating is disclosed. The system comprises an ultrasonic wedge having a back wall, a probe comprising a phased array transducer, wherein the probe is mounted to a probe interface wall of the ultrasonic wedge, and an ultrasonic inspection station connected to the probe by a probe cable, wherein the ultrasonic inspection station comprises a display, a microprocessor, a memory coupled to the microprocessor, and one or more executable instructions stored in the memory and configured to be executed by the processor, the executable instructions including instructions for displaying a first ultrasonic signal gate on the display, wherein the first ultrasonic signal gate is based on a theoretical Z distance between a first transducer element of the phased array transducer of the probe and a back wall of the ultrasonic wedge, and a theoretical Z distance between a last transducer element of the phased array transducer of the probe and the back wall of the ultrasonic wedge, locating a second ultrasonic signal gate above a start of the first ultrasonic signal gate, firing an ultrasonic signal from each of the transducer elements, identifying each of the transducer elements that did not trigger the first ultrasonic signal gate as dead transducer elements, and identifying each of the transducer elements that triggered the first ultrasonic signal gate and also triggered the second ultrasonic signal gate as dead transducer elements.

In another embodiment, a method for calibrating an ultrasonic wedge and a probe having a phased array transducer is disclosed. The method comprises the steps of automatically determining an ultrasonic signal acquisition width based on a first plurality of theoretical parameters of the ultrasonic wedge and the phased array transducer of the probe, and automatically determining a location of a first ultrasonic signal gate based on a second plurality of theoretical parameters of the ultrasonic wedge and the phased array transducer of the probe.

In yet another embodiment, the method for calibrating comprising the steps of automatically determining a location of a first ultrasonic signal gate based on a first plurality of theoretical parameters of the ultrasonic wedge and the phased array transducer of the probe, automatically determining an operating status of each of the transducer elements in the phased array transducer of the probe, wherein the operating status of a transducer element is determined to be live or dead, measuring an actual time of flight for each of the live transducer elements, and automatically determining at least one actual parameter of the ultrasonic wedge and the phased array transducer of the probe based on the actual time of flight for each of the live transducer elements.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
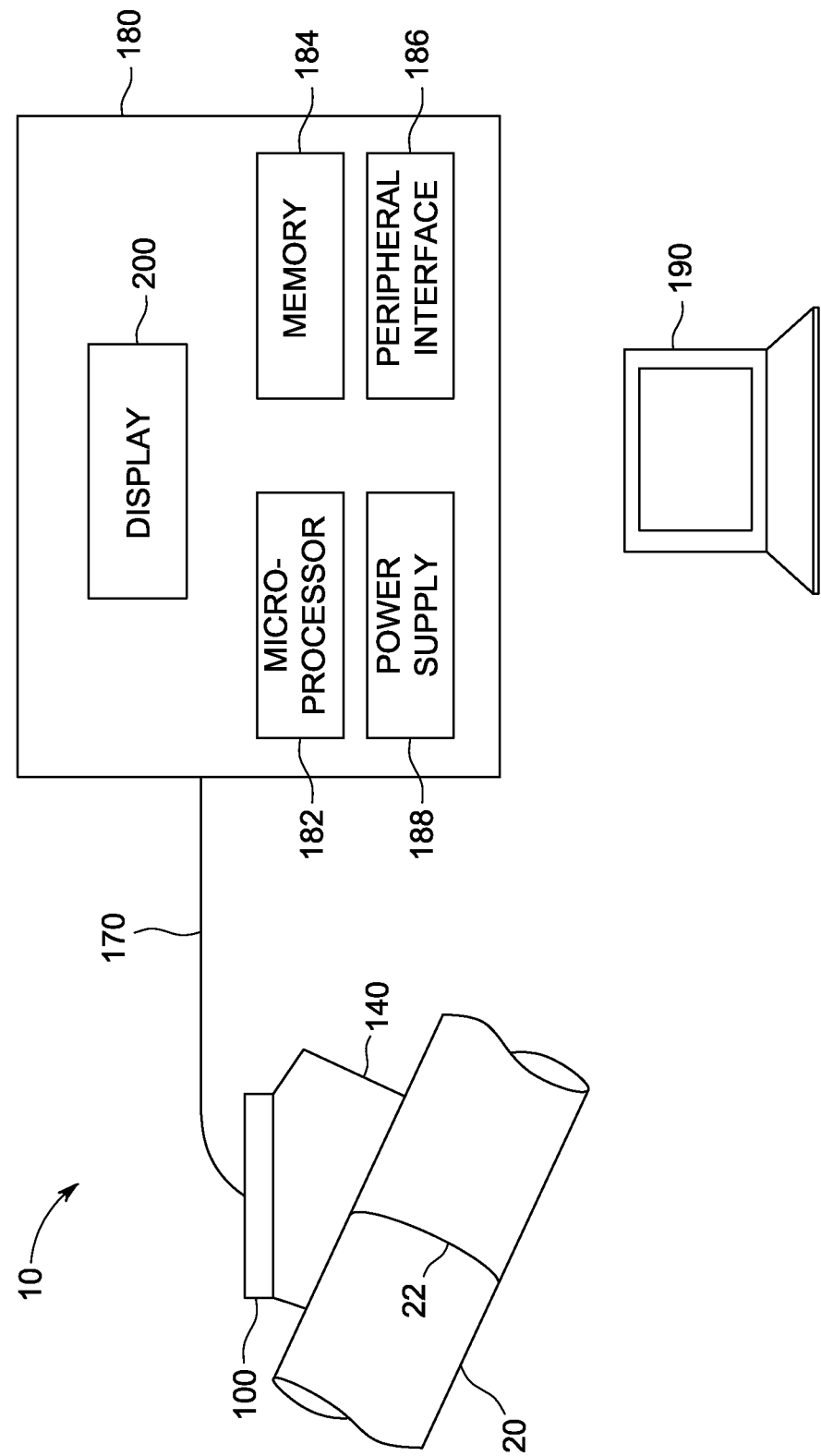
FIG. 1 is a block diagram of an exemplary ultrasonic testing system.
Figure 2:
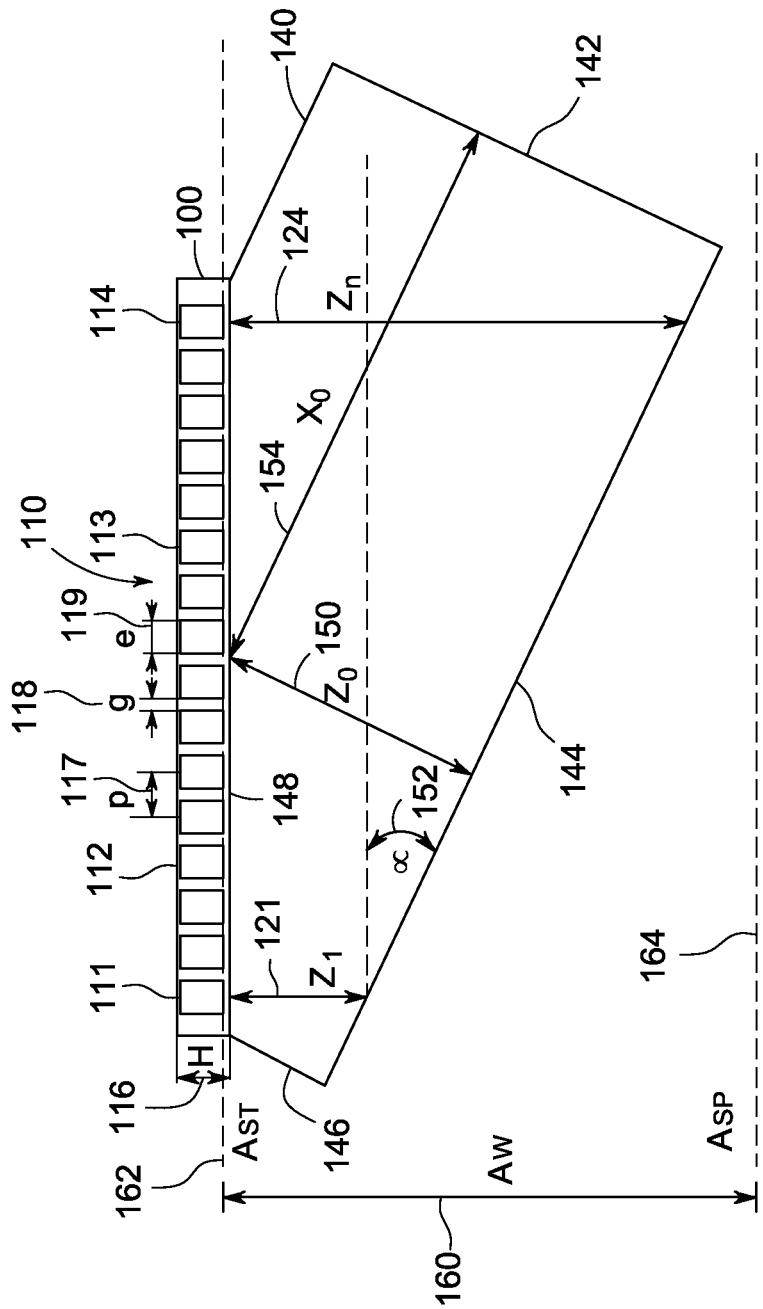
FIG. 2 illustrates an exemplary combination of a probe and an ultrasonic wedge.

FIG. 1 is a block diagram of an exemplary ultrasonic testing system 10. In one embodiment, the ultrasonic testing system 10 is used to inspect a test object (e.g., the weld 22 of a conduit 20). The ultrasonic testing system 10 can comprise a probe 100, that can include an array of ultrasonic transducer elements (i.e., in a phased array transducer 110) (as shown in FIG. 2). The probe 100 can be mounted on an ultrasonic wedge 140 that can be attached to the test object. The ultrasonic wedge 140 can be made from any material that has an acoustic velocity different from that of the test object. For example, some ultrasonic wedges are made from plastics such as plexi-glass or a polystyrene material through which sound travels at a known velocity. The amplitude and firing sequence of the individual transducer elements of the phased array transducer 110 can be controlled in order to adjust the angle and penetration strength of the ultrasonic signal that is sent into the test object.

A probe cable 170 can connect the probe 100 to an ultrasonic inspection station 180, which can include one or more microprocessor(s) 182 for running system software and controlling system operations, and memory 184 coupled to the microprocessor 182. Computer program instructions (executable instructions) can be stored in memory 184 or available to be executed by the microprocessor (e.g., downloadable from a network) 182 can make up all or a portion of the software and software packages discussed herein. The ultrasonic inspection station 180 can also comprise a display 200 for viewing system operations and inspection results. Electronics in the ultrasonic inspection station 180 can transmit and receive ultrasonic signals. The received signals are typically processed through some type of analog to digital conversion, after which they are displayed as A-scans with amplitude on the y axis and time of flight on the x axis. These digital signals form the signature of a potential anomaly and are typically stored in memory 184 and post processed to provide additional views for the operator to assist in determining if an anomaly is truly a defect or not. The microprocessor 182 can provide control over the entire process. The ultrasonic inspection station 180 can also include a power supply 188, connected to an external power supply (e.g., AC voltage between 90V and 240V) or provided by rechargeable batteries.

The ultrasonic inspection station 180 can also include peripheral interfaces 186 for managing data being sent between the ultrasonic inspection station 180 and other components. For example, in one embodiment, the peripheral interfaces 186 can include a USB, Ethernet (LAN), or wireless interface (WLAN) for receiving and loading an inspection plan prepared on a computer 190 remote from the test object and validated by an ultrasonic expert. This allows the inspection plan to be validated by an ultrasonic expert and then carried out by a lower skilled inspection technician at the test object. While the remotely prepared inspection plan need not be prepared by the inspection technician, the calibration procedure of the probe 100 and the ultrasonic wedge 140 must still be performed at the test object. As will be described, the disclosed method allows the calibration procedure to be performed by an inspection technician having a lower level of ultrasonic skill.

Figure 3:
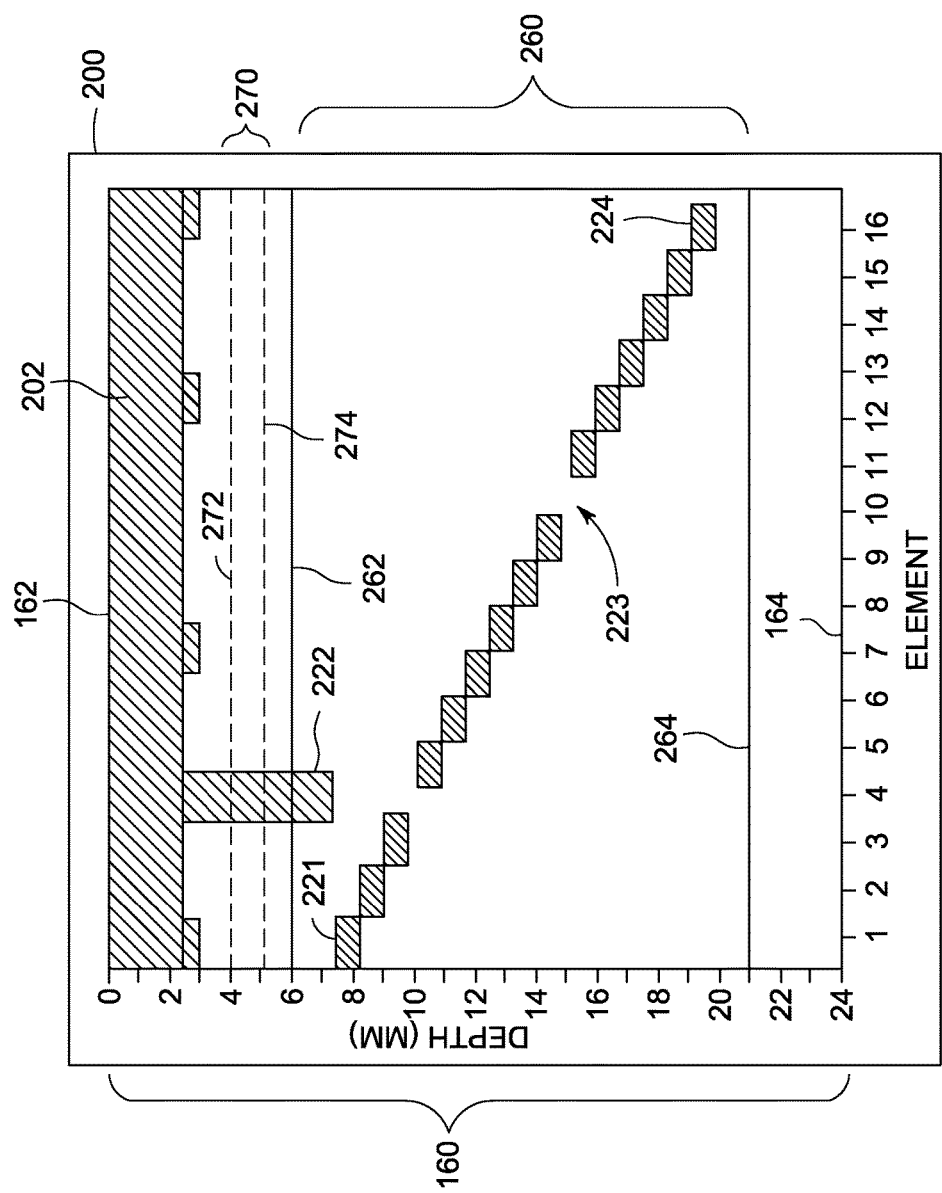
FIG. 3 illustrates an exemplary display of ultrasonic signals captured during the calibration of the probe and the ultrasonic wedge of FIG. 2.
Figure 4:
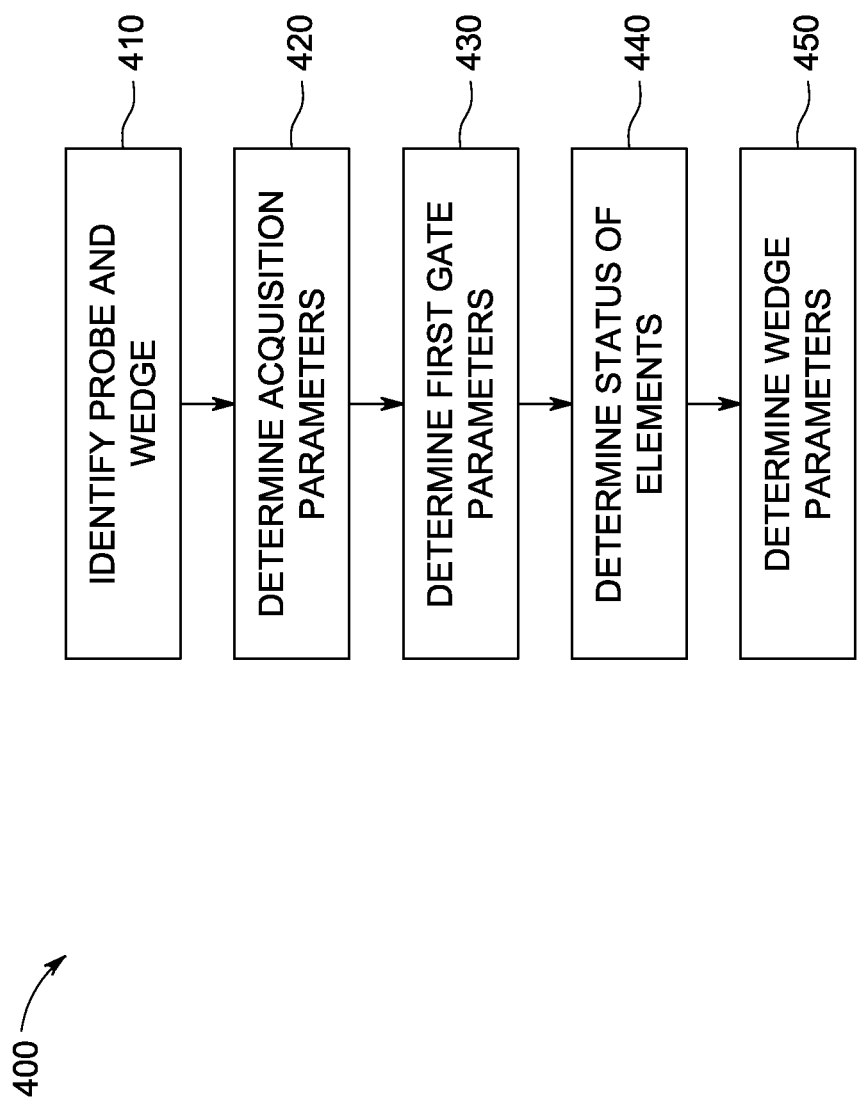
FIG. 4 is an exemplary method for calibrating the probe and the ultrasonic wedge of FIG. 2.

FIG. 2 illustrates an exemplary combination of a probe 100 and an ultrasonic wedge 140. FIG. 3 illustrates an exemplary display of ultrasonic signals captured during the calibration of the probe 100 and the ultrasonic wedge 140 of FIG. 2. FIG. 4 is an exemplary method 400 of calibrating the probe 100 and the ultrasonic wedge 140 of FIG. 2.

The exemplary phased array transducer 110 of the probe 100 of FIGS. 1 and 2 comprises sixteen transducer elements (n=16), including, e.g., a first transducer element 111, a fourth transducer element 112, an eleventh transducer element 113, and a last (sixteenth or nth) transducer element 114. It will be understood that phased array transducers 110 with more or less transducer elements can also be used. The parameters of the phased array transducer 110 can include the height of the transducer elements (H) 116, the pitch or center to center distance between two adjacent transducer elements (P) 117, the gap between adjacent transducer elements (g) 118, and the width of the individual transducer elements (e). The probe 100 is mounted to an exemplary ultrasonic wedge 140, having opposing first 142 and second 146 side walls, a back wall 144, and a probe interface wall 148. The parameters of the ultrasonic wedge 140 can include the Z offset ($Z_O$) 150, which is the distance between the center of the phased array transducer 110 and the ultrasonic wedge back wall 144, normal to the ultrasonic wedge back wall 144. The parameters of the ultrasonic wedge 140 can include the X offset ($X_O$) 154, which is the length or distance of a line between the center of the phased array transducer 110 and the ultrasonic wedge first sidewall 142, normal to the first side wall 142. In addition, the parameters of the ultrasonic wedge 140 include the ultrasonic wedge angle (a) 152, which is the angle between the ultrasonic wedge back wall 144 and the probe interface wall 148.

As part of the exemplary calibration method 400 of FIG. 4, the inspection technician can use the ultrasonic inspection station 180 at step 410 to identify the particular probe 100 (thereby identifying the phased array transducer 110) and ultrasonic wedge 140 being used. In one embodiment, the inspection technician can be prompted by the ultrasonic inspection station 180 to select the particular probe 100 and ultrasonic wedge 140 from a list of devices. In another embodiment, the ultrasonic inspection station 180 can automatically identify the probe 100. Once the probe 100 and the ultrasonic wedge 140 have been identified, the ultrasonic inspection station 180 can retrieve (e.g., from memory 184) the theoretical parameters for those devices to perform the calibration.

At step 420 of the exemplary calibration method 400, the ultrasonic inspection station 180 can determine the ultrasonic signal acquisition width ($A_W$) 160 (i.e., distance (mm) or time (s) between the acquisition start ($A_{ST}$) 162 and the acquisition stop ($A_{SP}$) 164) to be displayed (FIGS. 2 and 3) such that the ultrasonic inspection station 180 acquires the ultrasonic signal up to the theoretical maximum Z distance ($Z_{max}$) of the ultrasonic wedge 140. This determination can be made based on the theoretical parameters of the phased array transducer 110 of the probe 100 and the ultrasonic wedge 140. In one embodiment, the ultrasonic inspection station 180 can determine the ultrasonic signal acquisition parameters (e.g., as shown in FIGS. 2 and 3) using the following equations, assuming an acquisition start ($A_{ST}$) 162 of 0.0 mm:

$$Z_{iTH} = (Z_{OTH}) + \sum_{i=1}^{i=n}\left[\left(\left(P \times \left(i - \frac{1}{2}\right)\right) - \left(\frac{n \times P}{2}\right)\right) \times \mathrm{Sin}(\alpha_{TH})\right] \quad (1)$$

$$Z_{max} = Z_{nTH} + \left[\left(\frac{3}{4}\right) \times \mathrm{ABS}((2 \times Z_{1TH}) - Z_{nTH})\right] \quad (2)$$

$$\mathrm{If}(Z_{max} \leq Z_{nTH}) \rightarrow A_W = 1.25 \times Z_{nTH} \quad (3)$$
$$\mathrm{Else} \rightarrow A_W = Z_{max}$$

$$A_{SP} = A_W - A_{ST} \quad (4)$$

Where
n=number of transducer elements in the phased array transducer 110;
i=transducer element number from 1 to n;

$Z_{iTH}$=theoretical Z distance (material depth) between the $i^{th}$ transducer element to the ultrasonic wedge back wall 144;
$Z_{1TH}$=theoretical Z distance 121 of the first transducer element 111;
$Z_{nTH}$=theoretical Z distance 124 of the last transducer element 114;
$Z_{OTH}$=theoretical Z offset 150 defined for the ultrasonic wedge 140;
$\alpha_{TH}$=theoretical wedge angle 152 defined for the ultrasonic wedge 140;
P=pitch or center to center distance between two adjacent transducer elements 117;
$Z_{max}$=theoretical maximum Z distance of the ultrasonic wedge 140;
$A_{ST}$=acquisition start 162;
$A_{SP}$=acquisition stop 164; and
$A_W$=ultrasonic signal acquisition width 160.

By automatically determining the ultrasonic signal acquisition parameters, the ultrasonic inspection station 180 simplifies the calibration procedure and avoids the need for an inspection technician with a high level of ultrasonic skill and knowledge.

At step 430 of the exemplary calibration method 400, the ultrasonic inspection station 180 can determine the start 262 of a first ultrasonic signal gate 260 (or A Gate) and the stop 264 of the first ultrasonic signal gate 260 during which the ultrasonic signals above a certain threshold (e.g., first ultrasonic signal gate threshold of 80% of the height of the display 200) will be analyzed during the calibration procedure. This determination of the location of the first ultrasonic signal gate 260 can be made based on the theoretical parameters of the phased array transducer 110 of the probe 100 and the ultrasonic wedge 140. As shown in FIG. 3, the first ultrasonic signal gate 260 can be located such that the start 262 of the first ultrasonic signal gate 260 is located above and proximate the theoretical Z distance 121 (material depth) from the first transducer element 111 to the ultrasonic wedge back wall 144 (FIG. 2), and the stop 264 of the first ultrasonic signal gate 260 is located below and proximate the theoretical Z distance 124 from the last transducer element 114. The start 262 of the first ultrasonic signal gate 260 can also be located far enough below the initial pulse signals 202 to avoid inadvertently capturing the initial pulse signals 202. In one embodiment, the ultrasonic inspection station 180 can determine the parameters of the first ultrasonic signal gate 260 (as shown in FIG. 3) using the following equations:

$$\mathrm{FirstGateStart} = \tfrac{1}{3} \times Z_{1TH} \quad (5)$$

$$\mathrm{FirstGateStop} = Z_{nTH} + [(\tfrac{1}{2}) \times (A_W - Z_{nTH})] \quad (6)$$

$$\mathrm{FirstGateWidth} = \mathrm{FirstGateStop} - \mathrm{FirstGateStart} \quad (7)$$

By automatically determining the parameters of the first ultrasonic signal gate 260 during the calibration method 400, the ultrasonic inspection station 180 simplifies the calibration procedure and avoids the need for an inspection technician with a high level of ultrasonic skill and knowledge.

At step 440 of the exemplary calibration method 400, the ultrasonic inspection station 180 can determine the operating status of the individual transducer elements of the phased array transducer 110. A transducer element is not operating properly (or "dead") if, e.g., its wiring is disconnected or the wiring is short circuited. The presence of dead elements in the transducer can result in differences between the actual and theoretical parameters of the phased array transducer 110 of the probe 100 and the ultrasonic wedge 140.

In order to determine the operating status of each of the transducer elements (i.e., live or dead), the transducer elements can be individually tested by firing an ultrasonic signal from each of the transducer elements at 0°. If the wiring for a transducer element is disconnected, the firing of that transducer element will not trigger the first ultrasonic signal gate 260 as there will be no signal above the first ultrasonic signal gate threshold (e.g., 80%) in the first ultrasonic signal gate 260 (see FIGS. 2 and 3 where a back wall echo 223 in the first ultrasonic signal gate 260 is missing from the eleventh transducer element 113). If a transducer element (e.g., eleventh transducer element 113) does not trigger the first ultrasonic signal gate 260, it can be considered a dead transducer element.

If the wiring for a transducer element is short circuited, however, the initial pulse signal 202 for that transducer element may trigger the first ultrasonic signal gate 260 even though the transducer element is not operating properly (see FIGS. 2 and 3 where a back wall echo in the first ultrasonic signal gate 260 is missing from the fourth transducer element 112, but the first ultrasonic signal gate 260 is still triggered by the initial pulse signal 222 which extends into and triggers the first ultrasonic signal gate 260). So even though the short circuited transducer element (e.g., fourth transducer element 112) did trigger the first ultrasonic signal gate 260 with a signal above the first ultrasonic signal gate threshold (e.g., 80%) in the first ultrasonic signal gate 260 from firing that transducer element, it should not be considered a "live" or properly operating transducer element.

In order to determine the operating status of transducer elements by identifying transducer elements that have been short circuited, the ultrasonic inspection station 180 can determine the start 272 of a virtual or second ultrasonic signal gate 270 (or B Gate) and the stop 274 of the second ultrasonic signal gate 270 during which the ultrasonic signals above a certain threshold (e.g., second ultrasonic signal gate threshold of 80% of the height of the display 200) will be analyzed during the calibration procedure. This determination of the location of the second ultrasonic signal gate 270 can be made based on the theoretical parameters of the phased array transducer 110 of the probe 100 and the ultrasonic wedge 140. As shown in FIG. 3, the second ultrasonic signal gate 270 can be located such that the stop 274 of the second ultrasonic signal gate 270 is located above and proximate the start 262 of the first ultrasonic signal gate 260 and the start 272 of the second ultrasonic signal gate 270 is located above and proximate the stop 274 of the second ultrasonic signal gate 270. The start 272 of the second ultrasonic signal gate 270 can also be located far enough below the initial pulse signals 202 to avoid inadvertently capturing the initial pulse signals 202 from live transducer elements. In one embodiment, since the second ultrasonic signal gate 270 is used only to determine the operating status of the transducer elements in step 440, it may not be shown on the display 200 of the ultrasonic inspection station 180. In one embodiment, the ultrasonic inspection station 180 can determine the parameters of the second ultrasonic signal gate 270 (as shown in FIG. 3) using the following equations:

$$SecondGateStop = FirstGateStart - \left(\frac{C_W[mm/\mu s]}{F_P[MHz]}\right) \quad (8)$$

$$SecondGateStart = SecondGateStop - \left(2 \times \frac{C_W[mm/\mu s]}{F_P[MHz]}\right) \quad (9)$$

$$SecondGateWidth = SecondGateStop - SecondGateStart \quad (10)$$

$$\text{IF}\left(SecondGateStop[mm] <= 2 \times \frac{C_W[mm/\mu s]}{F_P[MHz]}\right) \quad (11)$$

$\rightarrow SecondGateStop[mm] = FirstGateStart[mm]$
$\rightarrow SecondGateStart[mm] = 0 \text{ mm}$ Where
$C_W$=theoretical velocity of sound in the ultrasonic wedge 140 (mm/μs); and
$F_P$=frequency of the phased array transducer 110 of the probe 100 (MHz).

The location of the second ultrasonic signal gate 270 (separated from the initial pulse signals 202 and just below the start 262 of the first ultrasonic signal gate 260) is chosen to identify a short circuited transducer element that triggers the first ultrasonic signal gate 260 based on the initial pulse signal 202 from that transducer element by determining if that transducer element also triggers the second ultrasonic signal gate 270. If a transducer element (e.g., fourth transducer element 112) triggers both the first ultrasonic signal gate 260 and the second ultrasonic signal gate 270, it can be considered a dead transducer element.

After identifying the dead transducer elements (e.g., short circuited fourth transducer element 112 and disconnected eleventh transducer element 113), the ultrasonic inspection station 180 can determine a list of live transducer elements (i=1 to $n_{live}$) that can be used to determine the actual (versus theoretical) parameters of the ultrasonic wedge 140 at step 450 of the exemplary calibration method 400. In one embodiment, the actual time of flight (TOF) of each of the live transducer elements (e.g., to and from the transducer element) can be measured and converted into actual Z distances (material depths) between the transducer element and the ultrasonic wedge back wall 144. In addition, the actual horizontal offset distance for each transducer element from the first transducer element 111 can be calculated based on the pitch 117 of the phased array transducer 110. In one embodiment, the ultrasonic inspection station 180 can use the measured actual Z distances and horizontal offset distances from the live transducer elements (i=1 to $n_{live}$) to determine the actual ultrasonic wedge Z offset ($Z_{OACT}$) 150, the actual ultrasonic wedge angle ($\alpha_{ACT}$) 152, and the actual orientation of the probe 100 using the following equations. Since the signals from each transducer element will be distributed linearly, linear regression can be used to compute these actual values.

$$y(x) = ax + b \quad (12)$$

$$\sum_{i=1}^{n_{live}} x_i = \left(i - \frac{1}{2}\right) \times P \quad (13)$$

$$\sum_{i=1}^{n_{live}} y_i = C_W \times \frac{TOF_i}{2} \quad (14)$$

$$a = \frac{\sum_{i=1}^{n} x_i y_i - n_{live}\overline{xy}}{\sum_{i=1}^{n} x_i^2 - n_{live}\overline{x}^2} \quad (15)$$

$$b = \overline{y} - a\overline{x} \quad (16)$$

-continued $$Z_{OACT} = \frac{(ax_1 + b) + (ax_n + b)}{2} \quad (17)$$

$$\alpha_{ACT} = Sin^{-1}[a] \quad (18)$$

$$IF(\alpha_{ACT} \geq 0) \rightarrow \{ProbeOrientation = \text{NORMAL}\} \quad (19)$$
$$ELSE \rightarrow \{ProbeOrientation = \text{REVERSED}\}$$

Where
i=List of the live transducer elements from 1 to $n_{live}$;
$x_{1 \ to \ nlive}$=Pitch index for each live transducer element;
$x_1$=Pitch Index of the first live transducer element 111;
$x_n$=Pitch Index of last live transducer element 114.
$y_{1 \ to \ nlive}$=Measured Z-value for each live transducer element;
$Z_{OACT}$=actual Z-Offset 150 based on the measured TOF of each live transducer element;
$\alpha_{ACT}$=actual ultrasonic wedge angle 152 based on the measured TOF of each live transducer element; and
ProbeOrientation=actual orientation of the probe 100 (normal or reversed).

It should be noted that if the value of a is not between −1 and 1, the ultrasonic inspection station 180 can identify an invalid configuration and assign null values for the actual ultrasonic wedge Z offset ($Z_{OACT}$) 150, the actual ultrasonic wedge angle ($\alpha_{ACT}$) 152, and the actual orientation of the probe 100.

In view of the foregoing, embodiments of the method for calibration automatically provide ultrasonic signal acquisition parameters and parameters of ultrasonic signal gates to an inspector that is performing an inspection. A technical effect is to simplify the calibration method and avoid the need for an inspection technician with a high level of ultrasonic skill and knowledge. Embodiments of the method for calibration automatically provide actual values for parameters of the ultrasonic wedge 140 to account for dead transducer elements and wear of the ultrasonic wedge 140. A technical effect is to provide more accurate calibration and subsequent ultrasonic measurements.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
an ultrasonic wedge having a back wall;
a probe comprising a phased array transducer, wherein the probe is mounted to a probe interface wall of the ultrasonic wedge; and
an ultrasonic inspection station connected to the probe by a probe cable, wherein the ultrasonic inspection station comprises a display, a microprocessor, a memory coupled to the microprocessor, and one or more executable instructions stored in the memory and configured to be executed by the processor, the executable instructions including instructions for:
determining a first ultrasonic signal gate, wherein the first ultrasonic signal gate is determined by the processor based on a first theoretical Z distance $Z_{1TH}$ between a first transducer element of the phased array transducer of the probe and the back wall of the ultrasonic wedge, and a last theoretical Z distance $Z_{nTH}$ between a last transducer element of the phased array transducer of the ultrasonic probe and the back wall of the ultrasonic wedge;
displaying the first ultrasonic signal gate on the display;
locating a second ultrasonic signal gate above a start of the first ultrasonic signal gate;
firing an ultrasonic signal from each of the transducer elements;
determining an operating status of each transducer element in the phased array transducer of the probe as live or dead, wherein each of the transducer elements that did not trigger the first ultrasonic signal gate and each of the transducer elements that triggered the first ultrasonic signal gate and also triggered the second ultrasonic signal gate are determined to be dead transducer elements and the remaining transducer elements are determined to be live transducer elements; and
calibrating, based on the identification of the dead and live transducer elements, the ultrasonic wedge and probe.

2. The system of claim 1, the executable instructions including further instructions for:
measuring an actual time of flight between each of the live transducer elements and the back wall of the ultrasonic wedge; and
determining an actual Z distance between each of the live transducer elements and the back wall of the ultrasonic wedge based upon the corresponding measured time of flight.

3. The system of claim 2, the executable instructions including further instructions for:
determining, for each live transducer element, a horizontal offset distance from the first transducer element based upon a center to center distance between adjacent ones of the transducer elements; and
determining an actual ultrasonic wedge Z offset distance $Z_{OACT}$ between the center of the phased array transducer and the ultrasonic wedge back wall, based upon the horizontal offset distances of the live transducer elements and the actual Z distances of the live transducer elements.

4. The system of claim 2, the executable instructions including further instructions for:
determining, for each live transducer element, a horizontal offset distance from the first transducer element based upon a center to center distance between adjacent ones of the transducer elements; and
determining an actual ultrasonic wedge angle between an ultrasonic probe interface and the ultrasonic wedge back wall based upon the horizontal offset distances of the live transducer elements and the actual Z distances of the live transducer elements.

5. The system of claim 2, the executable instructions including further instructions for:
determining, for each live transducer element, a horizontal offset distance from the first transducer element based upon a center to center distance between adjacent ones of the transducer elements; and
determining an actual orientation of the ultrasonic probe based upon the horizontal offset distances of the live transducer elements and the actual Z distances of the live transducer elements.

6. A method for calibrating an ultrasonic wedge and a probe having a phased array transducer, the method comprising the steps of:
automatically determining an ultrasonic signal acquisition width based on a first plurality of theoretical parameters of the ultrasonic wedge and the phased array transducer of the probe;
automatically determining a location of a first ultrasonic signal gate based on the first plurality of theoretical parameters of the ultrasonic wedge and the phased array transducer of the probe; and
calibrating, based on the determined ultrasonic signal acquisition width and the determined location of the first ultrasonic signal gate, the ultrasonic wedge and probe;
wherein the first plurality of theoretical parameters comprises:
a theoretical Z offset distance $Z_{OTH}$ between the center of the phased array transducer and a back wall of the ultrasonic wedge;
a theoretical ultrasonic wedge angle between the back wall of the ultrasonic wedge and a wall of the ultrasonic wedge that interfaces with the probe;
a first theoretical Z distance $Z_{1TH}$ between a first transducer element of the phased array transducer of the ultrasonic probe and the back wall of the ultrasonic wedge; and
a last theoretical Z distance $Z_{nTH}$ between a last transducer element of the phased array transducer of the probe and the back wall of the ultrasonic wedge.

7. The method of claim 6, further comprising the step of automatically determining an operating status of each of the transducer elements in the phased array transducer of the probe, wherein the operating status of a transducer element is determined to be live or dead.

8. The method of claim 7, wherein the step of automatically determining an operating status of each of the transducer elements in the phased array transducer of the probe comprises:
automatically determining a location of a second ultrasonic signal gate based on a second plurality of theoretical parameters of the ultrasonic wedge and the phased array transducer of the probe, wherein the location of the second ultrasonic signal gate is above the location of the first ultrasonic signal gate;

firing an ultrasonic signal from each of the transducer elements;

determining, for each of the transducer elements, if the ultrasonic signal triggered the first ultrasonic signal gate;

identifying the transducer elements that did not trigger the first ultrasonic signal gate as dead transducer elements;

determining, for each of the transducer elements that triggered the first ultrasonic signal gate, if the ultrasonic signal also triggered the second ultrasonic signal gate; and identifying the transducer elements that triggered the first ultrasonic signal gate and also triggered the second ultrasonic signal gate as dead transducer elements.

9. The method of claim 8, wherein the second plurality of theoretical parameters of the ultrasonic wedge and the phased array transducer of the probe comprises:

the theoretical velocity of sound in the ultrasonic wedge; and the frequency of the phased array transducer of the probe.

10. The method of claim 9, further comprising the steps of:

identifying the ultrasonic wedge and the probe; and retrieving the first and second plurality of theoretical parameters for the ultrasonic wedge and probe.

11. The method of claim 8, further comprising the step of:

measuring an actual time of flight for each of the live transducer elements; and automatically determining at least one actual parameter of the ultrasonic wedge and the phased array transducer of the probe based on the actual time of flight for each of the live transducer elements.

12. The method of claim 11, wherein the at least one actual parameter is an actual Z offset distance $Z_{OACT}$ between the center of the phased array transducer and the back wall of the ultrasonic wedge.

13. The method of claim 11, wherein the at least one actual parameter is an actual ultrasonic wedge angle between the back wall of the ultrasonic wedge and the wall of the ultrasonic wedge that interfaces with the probe.

14. A method for calibrating an ultrasonic wedge and a probe having a phased array transducer, the method comprising the steps of:

automatically determining a location of a first ultrasonic signal gate based on a first plurality of theoretical parameters of the ultrasonic wedge and the phased array transducer of the probe;

automatically determining an operating status of each of the transducer elements in the phased array transducer of the probe based on the first ultrasonic signal gate, wherein the operating status of a transducer element is determined to be live or dead;

measuring an actual time of flight for each of the live transducer elements;

automatically determining at least one actual parameter of the ultrasonic wedge and the phased array transducer of the probe based on the actual time of flight for each of the live transducer elements; and calibrating, based on the determined at least one actual parameter, the ultrasonic wedge and the probe;

wherein the first plurality of theoretical parameters comprises:

a first theoretical Z distance $Z_{1TH}$ between a first transducer element of the phased array transducer of the probe and a back wall of the ultrasonic wedge; and a last theoretical Z distance $Z_{nTH}$ between a last transducer element of the phased array transducer of the probe and the back wall of the ultrasonic wedge.

15. The method of claim 14, wherein the step of automatically determining an operating status of each of the transducer elements in the phased array transducer of the probe comprises:

automatically determining a location of a second ultrasonic signal gate based on a second plurality of theoretical parameters of the ultrasonic wedge and the phased array transducer of the probe, wherein the location of the second ultrasonic signal gate is above the location of the first ultrasonic signal gate;

firing an ultrasonic signal from each of the transducer elements;

determining for each of the transducer elements if the ultrasonic signal triggered the first ultrasonic signal gate;

identifying the transducer elements that did not trigger the first ultrasonic signal gate as dead transducer elements;

determining for each of the transducer elements that triggered the first ultrasonic signal gate if the ultrasonic signal also triggered the second ultrasonic signal gate; and identifying the transducer elements that triggered the first ultrasonic signal gate and also triggered the second ultrasonic signal gate as dead transducer elements.

16. The method of claim 15, wherein the second plurality of theoretical parameters of the ultrasonic wedge and the phased array transducer of the probe comprise:

the theoretical velocity of sound in the ultrasonic wedge; and the frequency of the phased array transducer of the probe.

17. The method of claim 14, wherein the at least one actual parameter is an actual Z offset distance $Z_{OTH}$ between the center of the phased array transducer and the back wall of the ultrasonic wedge.

18. The method of claim 14, wherein the at least one actual parameter is an actual ultrasonic wedge angle between the back wall of the ultrasonic wedge and the wall of the ultrasonic wedge that interfaces with the probe.

19. The method of claim 14, wherein determining a location of the first ultrasonic gate further comprises the step of automatically determining an ultrasonic signal acquisition width based on the first plurality of theoretical parameters of the ultrasonic wedge and the phased array transducer of the probe, wherein first plurality of theoretical parameters further comprises a theoretical Z offset distance $Z_{OTH}$ between the center of the phased array transducer and a back wall of the ultrasonic wedge, and a theoretical ultrasonic wedge angle between the back wall of the ultrasonic wedge and a wall of the ultrasonic wedge that interfaces with the probe.

* * * * *